United States Patent [19]
White

[11] Patent Number: 6,008,430
[45] Date of Patent: Dec. 28, 1999

[54] THREE-DIMENSIONAL PROSTHETIC ARTICLES AND METHODS FOR PRODUCING SAME

[75] Inventor: Eugene W. White, Rossiter, Pa.

[73] Assignee: Interpore Orthopaedics, inc., Irvine, Calif.

[21] Appl. No.: 08/987,986

[22] Filed: Dec. 10, 1997

Related U.S. Application Data

[63] Continuation-in-part of application No. 08/542,846, Oct. 13, 1995, Pat. No. 5,728,510, which is a continuation of application No. 08/308,762, Sep. 19, 1994, Pat. No. 5,487,933, which is a continuation-in-part of application No. 08/134,260, Oct. 8, 1993, Pat. No. 5,455,100, which is a division of application No. 07/647,999, Jan. 30, 1991, Pat. No. 5,348,788.

[51] Int. Cl.⁶ .................................. A61F 2/02; A61F 2/28
[52] U.S. Cl. .................................. 623/11; 623/16; 623/18
[58] Field of Search .................................. 623/11, 16, 18, 623/66

[56] References Cited

U.S. PATENT DOCUMENTS

| | | |
|---|---|---|
| 3,852,832 | 12/1974 | McGhan et al. . |
| 3,890,107 | 6/1975 | White et al. . |
| 4,231,979 | 11/1980 | White et al. . |
| 4,673,409 | 6/1987 | Van Kampen . |
| 4,839,215 | 6/1989 | Starling et al. . |
| 4,865,603 | 9/1989 | Noiles . |
| 4,976,736 | 12/1990 | White et al. . |
| 4,978,355 | 12/1990 | Frey et al. . |
| 5,011,494 | 4/1991 | von Recum et al. . |
| 5,030,233 | 7/1991 | Ducheyne . |
| 5,053,264 | 10/1991 | Beretta . |
| 5,147,402 | 9/1992 | Bohler et al. . |
| 5,192,324 | 3/1993 | Kenna . |
| 5,222,987 | 6/1993 | Jones . |
| 5,282,861 | 2/1994 | Kaplan . |
| 5,342,919 | 8/1994 | Dickens, Jr. et al. . |
| 5,348,788 | 9/1994 | White . |
| 5,380,328 | 1/1995 | Morgan ...................................... 606/70 |
| 5,455,100 | 10/1995 | White . |
| 5,487,933 | 1/1996 | White . |
| 5,496,372 | 3/1996 | Hamamoto et al. ...................... 623/16 |

*Primary Examiner*—Mickey Yu
*Assistant Examiner*—Dinh X. Nguyen
*Attorney, Agent, or Firm*—Hopgood, Calimafde, Kalil & Judlowe, LLP

[57] ABSTRACT

A three-dimensional porous mesh structure is prepared from a two-dimensional sheet form having a unique arrangement of main and secondary troughs on a first surface, and openings extending therethrough. The arrangement of troughs and openings creates an elaborate matrix of pores when the two-dimensional sheet is formed into the three-dimensional porous mesh structure which emulates osteon-evacuated bone.

10 Claims, 4 Drawing Sheets

THREE-DIMENSIONAL PROSTHETIC ARTICLES AND METHODS FOR PRODUCING SAME

RELATED APPLICATIONS

This is a continuation-in-part of Ser. No. 542,846 filed Oct. 13, 1995 (now U.S. Pat. No. 5,728,510) which is a continuation of Ser. No. 308,762 filed Sep. 19, 1994 (now U.S. Pat. No. 5,487,933) which is a continuation-in-part of Ser. No. 134,260 filed Oct. 8, 1993 (now U.S. Pat. No. 5,455,100) which is a divisional of Ser. No. 647,999 filed Jan. 30, 1991 (now U.S. Pat. No. 5,348,788).

FIELD OF THE INVENTION

The present invention generally relates to materials which simulate human tissue for use as prosthesis. More particularly, the invention is directed to novel three-dimensional structures made from select materials and processes for producing the three-dimensional structures from the select materials.

BACKGROUND OF THE INVENTION

Prosthetic materials are engineered elements which can achieve biological function when placed within a living organism. An important class of prosthetic materials are those which are used to repair and replace human body tissue such as osseous matter. To replace biological tissue in an acceptable, long lasting manner, the replacement materials must join with the surrounding living matter. Proper melding is achieved through the use of an appropriate material having a micro-network of capillaries permeating the structure to permit living tissue in-growth.

Such porous networks must be continuous, permitting unrestricted passage of blood and other body fluids from the surrounding tissue while also providing structural support. This can be easily envisioned in the design of artificial bone wherein osseous replacement materials must support the forces and stresses associated with the skeletal system and simultaneously allow passage of blood gases, nutrients, waste products and other extracellular material to and from the surrounding tissue.

In reconstructive surgery such as repair of highly comminuted fractures, healing can be accelerated by inclusion of materials having such porous matrix adjacent to the break point to enhance bone growth. Rebuilding of damaged long bones can also benefit from insertion of such porous prosthetic materials to re-achieve the desired pre-damage shape and strength.

Such porous yet semi-rigid materials are found in nature. For example, spiny starfish, certain sea urchins and coral exhibit a solid structure formed of calcium carbonate having a network of interconnecting pores and significant void volume in the form of a micro-porous matrix. Specifically, the slate pencil sea urchin has cigar-shaped protrusions that have a void volume of 50 percent and a porous structure with pore diameters of approximately 25 $\mu$m. Certain coral provide similar attributes with pore diameters of approximately 250–600 $\mu$m.

In the past, these aquatic materials were used to form biologically acceptable structures such as through hydrothermal treatment of the calcium carbonate skeletons to form hydroxyapatite. More detailed discussion of such techniques may be found in U.S. Pat. Nos. 3,890,107, 3,929,971, 4,231,979, 4,722,870 and 4,861,733, the teachings of which are all incorporated by reference herein.

Although these procedures offer a unique class of structures, they are accompanied by several significant drawbacks. The naturally forming aquatic structures are never completely uniform and often exhibit imperfections detrimental to surgical implantation. In addition, the materials are expensive to harvest, and such gleaning of nature has raised environmental impact concerns in some quarters.

These problems have led to a search for techniques to engineer and manufacture porous materials having specifically delineated structural properties in a controlled manner. For instance, U.S. Pat. Nos. 5,348,788 and 5,455,100 (the teachings of which are incorporated herein by reference) describe such porous articles having very specific, delineated structural properties referred to, in concept, as "minimal surface structures."

However, a problem has been recognized with minimal surface structures when used in orthopedic surgery/prosthetic applications. Minimal surface structures in three-dimensional arrays are "too regular" and not well received by orthopaedic surgeons. Technical difficulties in fabricating the ideal minimal surface structure include the exact registration of successive layers and the requirement of alternately placing successive layers "front-to-front" then "back-to-back." Thus, the known art still requires the exact registration of successive layers of two-dimensional sheets in un-natural, alternating layers to form a three-dimensional material which is too uniform and too regular for use as practical substitutes for natural bone.

U.S. Pat. No. 5,487,933 (the teachings of which are incorporated herein) covers the fabrication of a two-dimensional sheet structure that represents the basis for fabrication of an entirely new synthetic bone substitute material. The following description includes several important advancements which represent the next generation, three-dimensional bone-substitute material.

OBJECTS AND SUMMARY OF THE PRESENT INVENTION

It is an object of the present invention to provide a three-dimensional material which simulates human tissue for use in repair and replacement of osseous matter in the form of porous materials that have a network of interconnecting pores.

Another object of the present invention is to provide a three-dimensional material which simulates human osseous tissue for use as prosthesis in the form of porous materials that have a network of interconnecting pores and a void volume percent between 20 and 80.

It is another object of the present invention to provide a three-dimensional porous article with a substantially anisotropic distribution of pores wherein the pore diameter ranges between 25 and 2500 $\mu$m.

It is a further object of the present invention to provide biologically compatible, curable, bone-like compositions and three-dimensional structures made therefrom.

It is yet another object of the invention to provide biologically compatible hydroxyapatite, hydroxyapatite/collagen and hydroxyapatite/gelatin compositions and three-dimensional structures made therefrom.

It is a further object of the present invention to provide a bone substitute material which when properly configured simulates osteon evacuated cortical bone.

It is another object of the present invention to provide a method for manufacturing biologically compatible, curable, bone-like compositions and three-dimensional structures made from such compositions for use as cement in bone repair or as bone-substitute materials.

It is also another object of the invention to provide a method for making hydroxyapatite compositions, hydroxyapatite/collagen and hydroxyapatite/gelatin compositions and three-dimensional structures made from such compositions for use as cement in bone repair or as bone-substitute materials as tailored to specific system constraints.

The above and other objects of the present invention are realized in illustrative compositions suitable for use in repair of damaged bone and bone-simulating material comprising biologically compatible, curable, bone-like compositions such as hydroxyapatite, hydroxyapatite/collagen, hydroxyapatite/gelatin, and other bio-materials such as polyfunctional carboxylic acid substrates described in U.S. Pat. No. 4,218,255, calcium phosphate slurries and pastes described in U.S. Pat. No. 4,612,053, non-bioresorbable calcium phosphate described in U.S. Pat. No. 4,619,655, polymer based calcium phosphates described in U.S. Pat. No. 4,843,112, carbonated hydroxyapatite such as described in U.S. Pat. No. 4,880,610, organic acid-calcium phosphates described in U.S. Pat. No. 4,902,649, acidic phosphates described in U.S. Pat. No. 5,053,212, acidic citrates described in U.S. Pat. No. 5,149,368, polysaccharide calcium phosphates described in U.S. Pat. No. 5,180,426, calcium alkali-polyfunctional carboxylic acid substrates described in U.S. Pat. No. 5,218,035, calcium alkali-acidic citrates described in U.S. Pat. No. 5,262,166, calcium salts-polyfunctional acid substrates described in U.S. Pat. No. 5,281,265, and tannin/collagen-calcium phosphates described in WIPO Patent Publication Nos. WO 90/00892 and WO 90/01341, the teachings of which are all herein incorporated by reference.

A discussion of some of these materials may also be found in Stupp et al., *Organoapatites: Materials for Artificial Bone*, J. Biomedical Materials Res., Vol. 27, pages 301–311 (1993), the teachings of which is incorporated by reference herein.

Hydroxyapatite has a nominal composition of $Ca_{10}(PO_4)_6(OH)_2$ and comprises the principal mineral in human bones. The metal mold used in the forming process is machined by various surface shaping techniques that are known, such as computer guided milling, photolithography and electron discharge machining. Suitable mold metals include steel and brass and other rigid substrate materials well known to those skilled in the art.

A porous mesh suitable for emulating cortical bone structure can be made as follows. The mesh attributes are first formed in a master that is machined from metal sheets in a predetermined, scaled pattern on a specifically delineated surface area. From the metal masters are produced, by replication, as many "negative working masters" as desired.

The negative masters are made of silicone rubber or other suitable substitute materials evident to one skilled in these arts. With a light coating of mold release agent, whole sheets of replicas are retrieved. Silicone rubber is ideal for some applications but other applications may require more rigid materials. The silicone negative master is the inverted replica of the original metal master.

Bone substitute materials are subsequently produced from the silicone negative masters. Preferably, a mixture containing specific and predetermined amounts of water, gelatin and calcium phosphate are prepared at a set temperature. Bovine gelatin ($C_{76}H_{124}O_{29}N_{24}S_x$) can be used but any albumin usually obtained from boiling animal bones and cartilage under pressure with water are suitable. Collagen may also be added as an alternate or additional reagent. Collagen of the type contemplated herein includes a hydroxyproline, glycine-type protein which is the chief organic constituent of connective tissue and bones, which yields gelatin when steam autoclaved in water, and which is usually comprised of 50.75% carbon, 6.47% hydrogen and 17.86% nitrogen.

Such mixtures are applied warm with a suitable spatula to a selected silicone negative master and worked into the formed pattern. The assembly is then chilled for a predetermined time period allowing the gelatin to set. The gelled mix is released from the master and wrapped on a suitably shaped mandrel. The shape of the selected mandrel closely corresponds to the shape of the actual bone in the desired repair site. After the suitable shape is achieved, the hydroxyapatite material is slipped off the mandrel and allowed to dry.

The resulting shaped material must then be stabilized before use in the human body. Hydroxyapatite can be stabilized by known techniques such as thermal/vacuum processing or chemical cross-linking. Gelatin cross-link treatment renders the gelatin within the hydroxyapatite/gelatin composite less bio-degradable. Alternatively, the final process stage can be a high temperature burn off of the gelatin binder to sinter the hydroxyapatite body for strength. If such a burn off is contemplated, the starting materials should have a higher loading of calcium phosphate relative to the gelatin.

The three-dimensional prosthetic structure made from a non-woven porous mesh in sheet form of the present invention comprises a continuous two-dimensional sheet having a substantially uniform thickness between opposing sides, a series of substantially parallel and linked main troughs extending in one horizontal direction along a first side of the sheet, the main troughs having a depth in the sheet that extends substantially into the sheet. The main troughs are spaced from adjacent main troughs by a distance approximately ½ a width of the main trough with the main troughs further linked to co-linear troughs by a first series of secondary shallow troughs.

One or more small openings extends through the bottom of each main trough to a second side of the sheet. Such openings have a diameter that is approximately ⅓ the width of the main trough and a second series of secondary shallow troughs extends substantially perpendicular to and connects with the main troughs. The two-dimensional sheets have thickness ranging between 200 to 2000 microns, and the depth of the secondary troughs are approximately ½ the depth of the main troughs. The main troughs extend approximately 80 percent through the thickness of the two-dimensional sheets. The small openings have a diameter that is approximately equal to the width of the secondary troughs. The first series of secondary troughs extend substantially in parallel through the two-dimensional sheet and the second series of secondary troughs also extend substantially parallel through the sheet.

The three-dimensional prosthetic is a porous structure made, preferably, by wrapping the two-dimensional mesh around a mandrel having a select shape characteristic with the mesh being wrapped in multiple layers to form a network of three dimensional pores extending through-out the formed body. The layers of mesh can be adhesively bonded to adjacent layers.

The invention also includes a method of forming the three-dimensional prosthetic structure comprising the steps of:

(a) making a primary form corresponding in shape to a two-dimensional mesh structure;

(b) casting a negative form of the two-dimensional mesh structure by placing a curable material in fluid state into the primary form, allowing the material to cure and removing the cured negative form from the primary form;

(c) casting a two-dimensional mesh by placing a mesh material in the negative form and allowing the mesh material to partially cure;

(d) removing the mesh material from the negative form before the mesh material is completely cured; and (e) forming a shaped body having a three-dimensional pore structure.

The preferred method further comprises wrapping the mesh material around a shape defining mandrel and completing mesh curing while on the shape-defining mandrel. Other methods of forming a multi-layered, three-dimensional structure include stacking of the mesh material one above the other or wrapping the mesh material onto itself.

The primary form of step (a) is made by machining a metal sheet which is preferably made of brass, and the curable material of step (b) is preferably made of silicone rubber. The mesh material of step (c) is preferably warmed from about 60° C. to about 80° C. The mesh material of step (c) is preferably tricalcium phosphate $(Ca)_3(PO_4)_2/(Ca)_3(PO_4)_3$ and gelatin at 45 wt. % $H_2O$, 47 wt. % tricalcium phosphate powder and 8 wt. % gelatin.

Preferably, the partially cured mesh material of step (d) is chilled to about 3° C. to form a gel mix, and the gel mix is peeled from the negative form, trimmed and wrapped on the desired mandrel simulating a target three-dimensional prosthetic structure.

The method can further comprise a drying step after removing the three-dimensional prosthetic structure from the mandrel. The three-dimensional prosthetic structure is allowed to achieve a temperature of about 50° C., charred at about 250° C. for about two hours to pyrolyze the gelatin, and fired at about 1150° C. for about two hours to completely burn off the gelatin and sinter the final hydroxyapatite product.

The foregoing features of the present invention may be more fully appreciated by reference to the following detailed description of the specific embodiments thereof, in conjunction with the associated figures.

DETAILED DESCRIPTION OF THE PRESENT INVENTION

The present invention is directed to the preparation of a new man made structure comprised of materials suitable for use in repair of damaged bone and bone-simulating material comprising biologically compatible, curable, bone-like compositions such as hydroxyapatite, hydroxyapatite/collagen, hydroxyapatite/gelatin, and other bio-materials such as described in the above-noted patents.

The Basic 2-D Sheet

The two-dimensional (2-D) sheet structure is specifically designed for assembly into a variety of shapes, not just rectangular blocks, that more closely correspond to the shapes of the actual bone in many repair sites such as hollow cylindrical or doubly curved plate shapes. The porous 2-D mesh sheets provide the basis for a three-dimensional (3-D) structure that closely emulates the anisotropic network associated with cortical bone mass.

Figure 1:
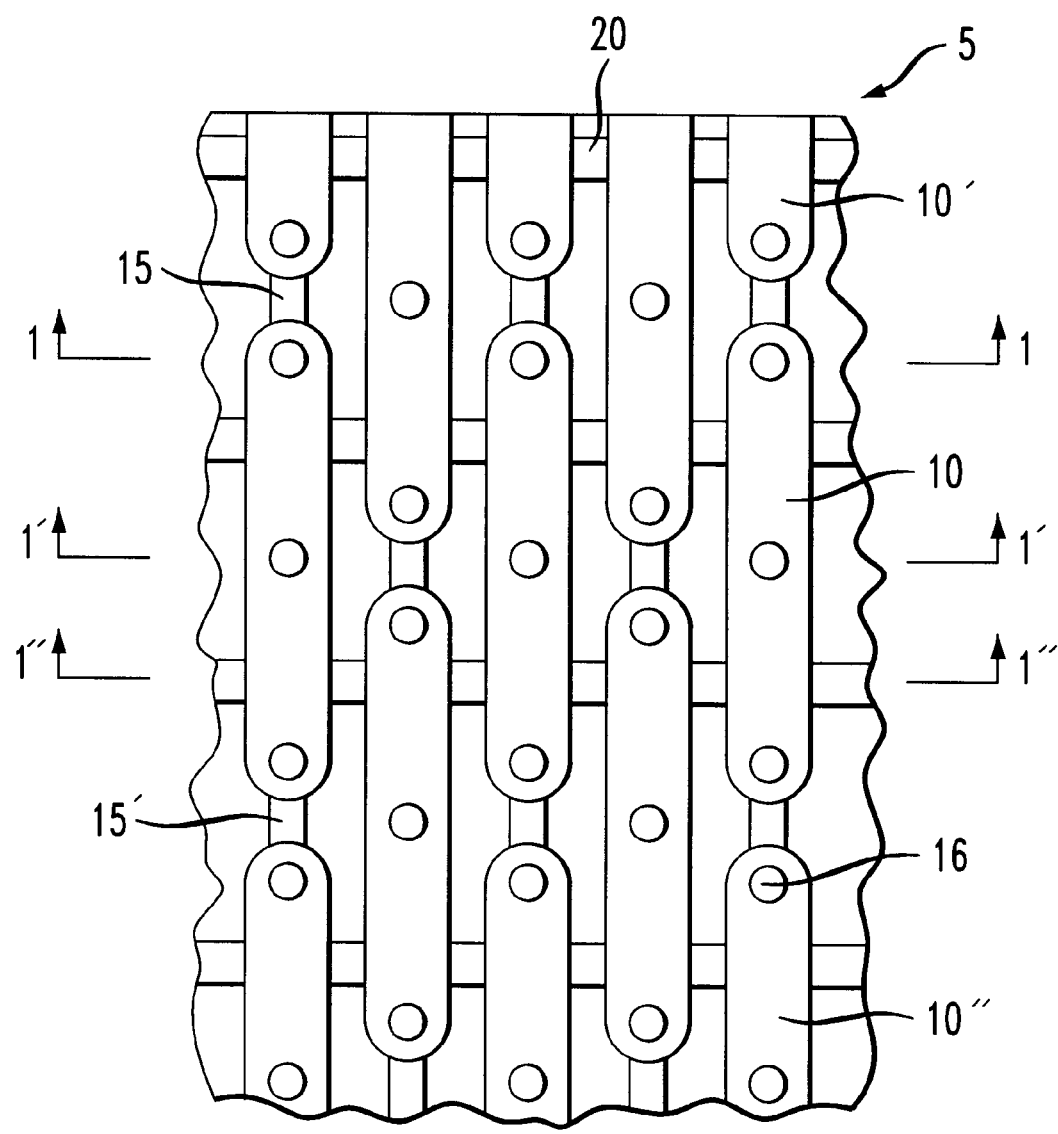
FIG. 1 depicts a plan view of the two-dimensional sheet structure of the present invention.

FIG. 1 depicts an exemplary two-dimensional structure of the present invention shown in scale at from 100 to 1000 $\mu m$ per division (squares in the figure). Two masters were machined to this sketch using a scale of 0.015 inches per division (375 $\mu m$). The masters were machined in 2.65×9 inch brass sheets with the pattern machined on an area of two by eight inches.

The brass masters are used to produce, by replication, as many "negative working masters" as desired. FIG. 1 shows a continuous sheet generally designated with the numeral 5 having a series of substantially parallel and linked main troughs 10 extending in one horizontal direction along the sheet, with each main trough 10 further linked to co-linear troughs 10' and 10" by a series of secondary shallow troughs 15 and 15'.

Each main trough (exemplified by trough 10) has one or more small openings 16 extending through the bottom of each main trough. Openings 16 have a diameter that is approximately ⅓ the width of main trough 10. FIG. 1 also shows a second series of secondary shallow troughs 20 extending perpendicular to and connecting the main troughs such as 10.

Figure 2A:
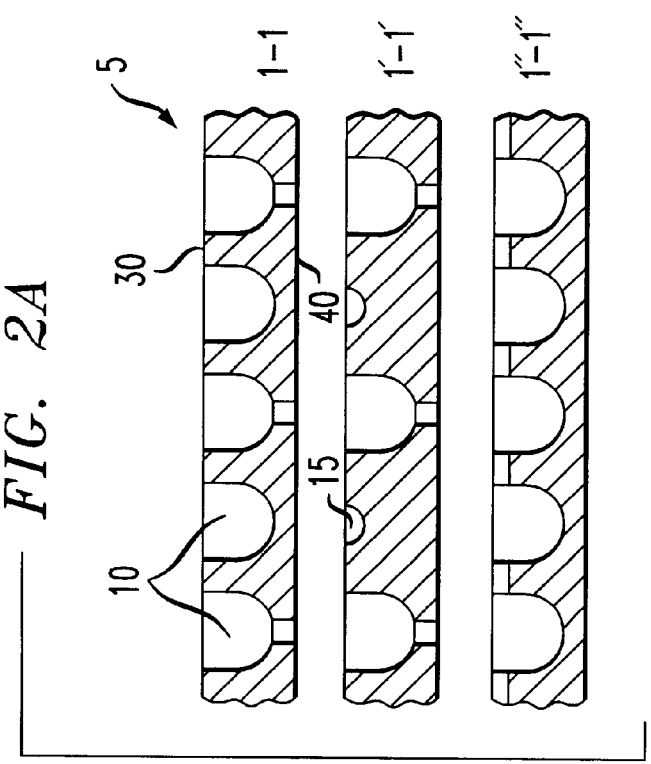
FIG. 2A provides a positive cross-sectional view of the two-dimensional sheet of FIG. 1, taken at planes 1—1, 1'—1' and 1"—1".

FIG. 2A provides a positive cross-sectional view of the sheet of FIG. 1, taken at planes 1—1, 1'—1' and 1"—1". Sheet 5 is shown as being a continuous sheet having a substantially uniform thickness between opposing sides 30 and 40. A series of substantially parallel and linked main troughs 10 extend in one horizontal direction along a first side 30 of sheet 5. Main troughs 10 have a depth in sheet 5 that extends substantially into the sheet with each main trough 10 spaced from adjacent main troughs by a distance approximately ½ a width of the main trough. Linking series of secondary shallow troughs 15 are also shown.

One or more small openings 16 are shown in FIG. 2A extending through the bottom of each main trough 10 into second side 40 of sheet 5. Openings 16 have a diameter that is approximately ⅓ the width of main trough 10.

Figure 2B:
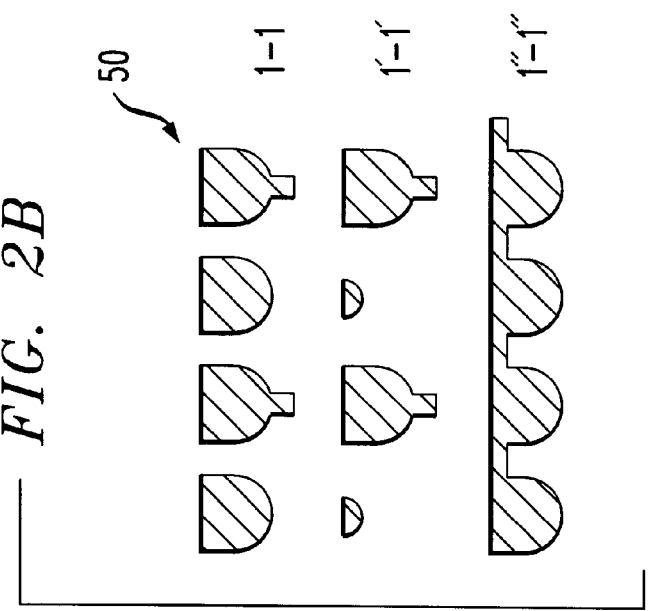
FIG. 2B provides a negative cross-sectional view of the two-dimensional sheet of FIG. 1, taken at planes 1—1, 1'—1' and 1"—1".

FIG. 2B provides a negative cross-sectional view of the sheet of FIG. 1, taken at planes 1—1, 1'—1' and 1"—1". Negative masters such as 50 shown in FIG. 2B can be made in silicone rubber. With only a light coating of mold release agent, whole sheet replicas are made with excellent fidelity. Silicone rubber is ideal for some applications but other applications may require more rigid materials.

Built-Up 3-D Structure

Bone substitute materials are made from the silicone negative masters such as depicted in FIG. 2B. For this a mixture containing 45 parts water, 8 parts gelatin and 47 parts tricalcium phosphate, $(Ca)_3(PO_4)_2/(Ca)_3(PO_4)_3$, was used. The mixture was prepared at 80° C. and the mix was applied hot with a Teflon spatula to the silicone master and worked into the structure. While still hot, the mix was manipulated such that it was uniformally in the structure and excess material was easily worked aside exposing the top surfaces of the protruding silicone structure.

Once in the silicone mold, the assembly was chilled in the refrigerator for about 10 minutes. This allowed the gelatin to set giving it good handling strength. The gelled mix easily completely released from the mold and was trimmed with scissors and wrapped on a wax paper covered mandrel (glass test tube). Just prior to wrapping on the mandrel, the one surface of the sheet was misted with water to produce the layer-to-layer gluing effect. The now cylinder-shaped assembly was slipped off the mandrel, the paper removed from inside the hollow cylinder and the part was allowed to dry in air overnight. It is important to remove the mandrel otherwise drydown shrinkage will produce cracks in the part and linear shrinkage will be distorted. As discussed above, the resulting part must be stabilized prior to use in body.

Figure 3A:
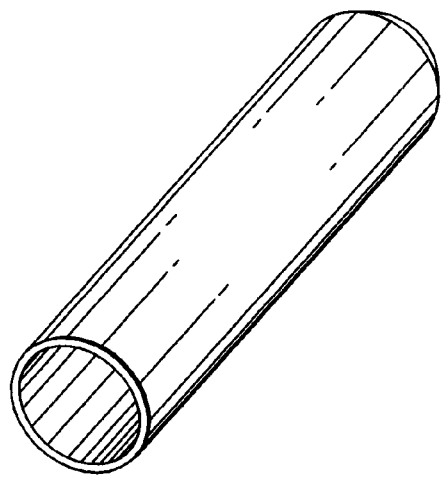
FIGS. 3A and 3B show two alternate ways of using a shaped mandrel to form a three-dimensional, shaped structure.
Figure 3B:
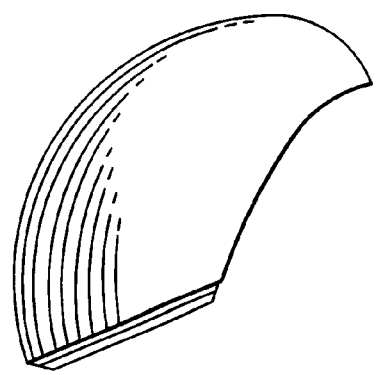

FIG. 3A shows a three-dimensional, shaped structure in the shape of a straight, hollow tube which was made on a glass test tube mandrel. Different and specific shapes for different parts of the skeletal system and for the different types of bone to-be-substituted can be thus made. For example, FIG. 3B shows a flat, slightly concave three-dimensional structure made from a mandrel in the shape of a portion of the human skull.

Figure 4:
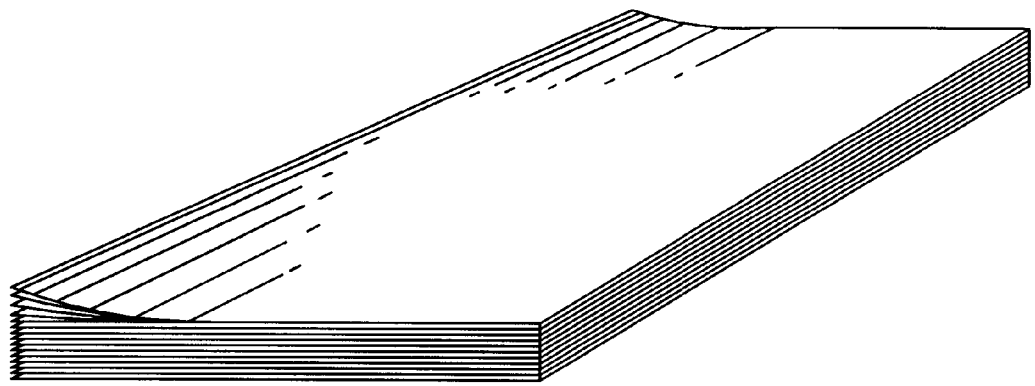
FIG. 4 depicts a three-dimensional rectangular block made by stacking two-dimensional mesh material one above the other.
Figure 5:
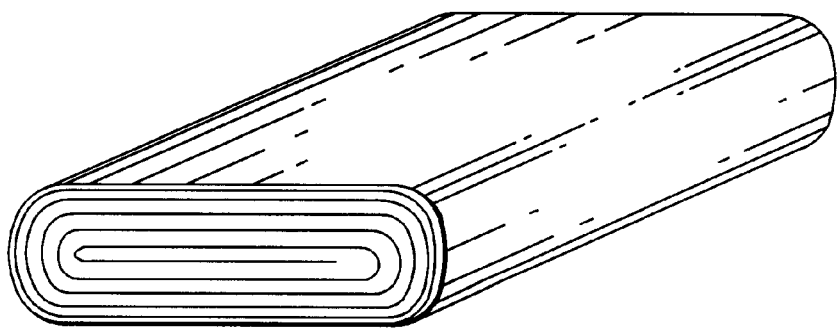
FIG. 5 shows a three-dimensional structure made by wrapping a two-dimensional mesh sheet onto itself.

FIG. 4 depicts a three-dimensional rectangular block made by stacking two-dimensional mesh material one above the other. Such structures can be used as substrates for further processing into the definitive shape desired by, for example, cutting with a wet diamond saw or using a machinist's lathe. FIG. 5 shows a three-dimensional structure made by wrapping a two-dimensional mesh sheet onto itself.

The following is the preferred fabrication steps for making the porous, 3-D hydroxyapatite structures.
1. Brass masters were machined on a computer-controlled milling machine to product the pattern shown in FIG. 1. The machined masters were fabricated with 1/64 inch holes and 1/32 inch wide grooves. The machined surface measured 2×8 inches. Such brass masters constitute the molds for making "working" negative masters.
2. The working negative masters are made by replicating the brass masters in silicone rubber. A caulking silicone (such as GE Silicone II black) was used, as an example.
3. A warm (about 60° C.) mix of tricalcium phosphate ("TCP"), $(Ca)_3(PO_4)_2$ or $(Ca)_3(PO_4)_3$, in gelatin having a nominal formulation of 45 wt. % $H_2O$, 47 wt. % TCP powder and 8 wt. % gelatin is worked into the warmed silicone negative. Deflashing operations are no longer necessary.
4. After the filled negative has been chilled in a 3° C. refrigerator, the gelled mix is peeled from the silicone mold, trimmed and wrapped on a suitable mandrel simulating the desired skeletal structure. Using a mandrel in the shape a desired skeletal structure, virtually any geometric or "free form" can be fabricated. Alternatively, the gelled mix can be peeled from the silicone mold, trimmed and simply rolled into a log shape as shown in FIG. 5 to form a cylindrical shape (in that case) or stacked into a block as shown in FIG. 4, for use as bone replacement parts.
5. After drydown to a finish drying temperature of about 50° C., the part is charred at 250° C. for two hours to pyrolyze the gelatin binder then fired at 1150° C. for two hours after a three hour ramp to temperature to completely burn off the gelatin char and sinter the hydroxyapatite. The sintering operation effectively "cements" the layers together and densifies the hydroxyapatite. There is about a 50% linear shrinkage of the part in going from the silicone mold dimension to the finished porous hydroxyapatite product. One skilled in the art will compensate for the shrinkage and reduction of the hole, lumen or channel dimensions to the desired scale for new bone ingrowth based on this disclosure.

The above-described arrangement is merely illustrative of the principles of the present invention. Numerous modifications and adaptations thereof will be readily apparent to those skilled in the art without departing from the spirit and scope of the present invention.

What is claimed is:

1. A three-dimensional prosthetic structure made from a non-woven porous mesh in sheet form, said mesh comprising:
    a continuous sheet having a substantially uniform thickness between opposing sides;
    a series of substantially parallel and linked main troughs extending in one horizontal direction along a first side of said sheet, said main troughs having a depth in said sheet that extends substantially into said sheet, said main troughs are spaced from adjacent main troughs by a distance approximately ½ a width of said main trough, said main troughs further linked to co-linear troughs by a first series of secondary shallow troughs;
    one or more small openings extending through the bottom of each main trough to a second side of said sheet, said openings having a diameter that is approximately ⅓ the width of said main trough; and
    a second series of secondary shallow troughs extending substantially perpendicular to and connecting said main troughs.

2. The three-dimensional prosthetic structure of claim 1, wherein the thickness of said sheet ranges between 200 to 2000 microns.

3. The three-dimensional prosthetic structure of claim 2 wherein the depth of said secondary troughs are approximately ½ the depth of said main troughs.

4. The three-dimensional prosthetic structure of claim 2 wherein said main troughs extend approximately 80 percent through said thickness of said sheet.

5. The three-dimensional prosthetic structure of claim 1 wherein said small openings have a diameter that is approximately equal to the width of said secondary troughs.

6. The three-dimensional prosthetic structure of claim 5 wherein said first series of secondary troughs extend substantially in parallel through said sheet.

7. The three-dimensional prosthetic structure of claim 6 wherein said second series of secondary troughs extend substantially parallel through said sheet.

8. The three-dimensional prosthetic structure of claim 1, wherein said porous three-dimensional body is formed by wrapping said mesh around a mandrel having a select shape characteristic, wherein said mesh is wrapped in multiple layers to form a network of three dimensional pores extending throughout said body.

9. The three-dimensional prosthetic structure of claim 1, wherein each said non-woven porous mesh is a two-dimensional sheet and wherein said two-dimensional sheets are stacked one above the other to form a multi-layered, three-dimensional structure.

10. The three-dimensional prosthetic structure of claim 1, wherein each said non-woven porous mesh is a two-dimensional sheet and wherein said two-dimensional sheetis wrapped onto itself to form a multi-layered, three-dimensional structure.

\* \* \* \* \*